US010799355B2

(12) United States Patent
He et al.

(10) Patent No.: US 10,799,355 B2
(45) Date of Patent: Oct. 13, 2020

(54) APICAL IMPLANTATION MITRAL VALVE BALLOON CLOSURE PLATE BLOCKING BODY AND IMPLANTATION METHOD

(71) Applicant: JIANGSU UNIVERSITY, Jiangsu (CN)

(72) Inventors: Zhaoming He, Jiangsu (CN); Teng Jing, Jiangsu (CN); Kailiang Zhang, Jiangsu (CN)

(73) Assignee: JIANGSU UNIVERSITY (CN)

( * ) Notice: Subject to any disclaimer, the term of this patent is extended or adjusted under 35 U.S.C. 154(b) by 260 days.

(21) Appl. No.: 16/093,926

(22) PCT Filed: Dec. 7, 2016

(86) PCT No.: PCT/CN2016/108784
§ 371 (c)(1),
(2) Date: Oct. 15, 2018

(87) PCT Pub. No.: WO2017/177700
PCT Pub. Date: Oct. 19, 2017

(65) Prior Publication Data
US 2019/0105156 A1   Apr. 11, 2019

(30) Foreign Application Priority Data
Apr. 14, 2016 (CN) .......................... 2016 1 0229741

(51) Int. Cl.
*A61F 2/24* (2006.01)
*A61B 17/00* (2006.01)
*A61B 17/04* (2006.01)

(52) U.S. Cl.
CPC ........ *A61F 2/2454* (2013.01); *A61B 17/0057* (2013.01); *A61F 2/24* (2013.01);
(Continued)

(58) Field of Classification Search
CPC .......................................... A61F 2/2442–2466
See application file for complete search history.

(56) References Cited

U.S. PATENT DOCUMENTS

| 4,692,164 A | 9/1987 | Dzemeshkevich et al. ...... 623/2 |
| 6,024,096 A * | 2/2000 | Buckberg .............. A61F 2/2478 128/898 |

(Continued)

FOREIGN PATENT DOCUMENTS

| CN | 103491902 | 1/2014 | ............... A61F 2/24 |
| CN | 104042359 | 9/2014 | ............... A61F 2/24 |

(Continued)

OTHER PUBLICATIONS

International Search Report and Written Opinion issued in PCT/CN2016/108784 dated Feb. 4, 2017, (English translation of Search Report) 16 pgs.

*Primary Examiner* — Shaun L David
(74) *Attorney, Agent, or Firm* — Hayes Soloway P.C.

(57) ABSTRACT

An apical implantation mitral valve balloon closure plate blocking body and an implantation method, for human heart repair are disclosed. A balloon closure plate made from an elastic plastic material which may be filled with a gas or a curable liquid is implanted via a small incision on the left side of the chest, enters the left ventricle via the apex, and is placed and fixed at a backflow hole position of a front and rear leaflet closure point of the mitral valve. The present disclosure treats diseases such as functional mitral valve regurgitation, and the success rate for repairing functional mitral valve backflow is more than 90%.

9 Claims, 5 Drawing Sheets

(52) U.S. Cl.
CPC ............ *A61F 2/246* (2013.01); *A61F 2/2466* (2013.01); *A61B 17/0401* (2013.01); *A61B 2017/00579* (2013.01); *A61B 2017/00592* (2013.01); *A61B 2017/00623* (2013.01); *A61B 2017/0464* (2013.01); *A61F 2210/0085* (2013.01); *A61F 2220/0016* (2013.01); *A61F 2250/0003* (2013.01)

(56) References Cited

U.S. PATENT DOCUMENTS

| | | | | |
|---|---|---|---|---|
| 8,932,348 | B2* | 1/2015 | Solem | A61F 2/246 623/2.11 |
| 2007/0270943 | A1* | 11/2007 | Solem | A61F 2/246 623/2.11 |
| 2010/0131057 | A1* | 5/2010 | Subramanian | A61F 2/2445 623/2.36 |
| 2010/0298929 | A1* | 11/2010 | Thornton | A61F 2/2445 623/2.1 |
| 2011/0029071 | A1* | 2/2011 | Zlotnick | A61B 17/00234 623/2.11 |
| 2011/0066233 | A1* | 3/2011 | Thornton | A61B 17/00234 623/2.11 |
| 2012/0253457 | A1 | 10/2012 | Winston et al. | 623/2.37 |
| 2014/0243968 | A1* | 8/2014 | Padala | A61F 2/246 623/2.36 |
| 2016/0089238 | A1 | 3/2016 | Centola et al. | A61F 2/2445 |
| 2017/0112618 | A1 | 4/2017 | Li et al. | A61F 2/24 |
| 2017/0151057 | A1 | 6/2017 | He et al. | A61F 2/24 |

FOREIGN PATENT DOCUMENTS

| | | | |
|---|---|---|---|
| CN | 104055605 | 9/2014 | ............ A61F 2/24 |
| CN | 105455924 | 4/2016 | ............ A61F 2/24 |
| CN | 105726072 | 7/2016 | ............ A61B 17/00 |

* cited by examiner

APICAL IMPLANTATION MITRAL VALVE BALLOON CLOSURE PLATE BLOCKING BODY AND IMPLANTATION METHOD

FIELD OF TECHNOLOGY

The invention refers to the field of human heart repair technology and medical devices, especially to an instrument which is capable of repairing mitral regurgitation.

BACKGROUND TECHNOLOGY

The heart and valves of human is shown in FIG. 1, the left ventricle 3 is located on the upper left side of the apex 4 of the heart, the mitral valve 2 is located between the left atrium 1 and the left ventricle 3, and the mitral valve 2 controls blood flow from the left atrium 1 to the left ventricle 3. Those dysfunctional mitral valves 2 will cause the insufficient closure of the leaflets, leading to the blood flow back from the left ventricle 3 to the left atrium 1 during systole. Mitral regurgitation will cause pulmonary congestion and hypertrophy of the left ventricle 3, eventually leading to the left heart failure and death.

The structure of the mitral valve 2 as shown in FIG. 2, the mitral valve 2 is a complicated one-way valve structure withstanding blood pressure, and composed of the annulus 2.1, the anterior leaflet 2.2, the posterior leaflet 2.3, the chordae tendineae 2.4, the papillary muscles 2.5 and the myocardium of the left ventricle. The papillary muscles 2.5 attach to the wall of the left ventricle, and the anterior leaflet 2.2 and posterior leaflet 2.3 attach to the annulus 2.1. The annulus is an internal tissue structure that connects the anterior leaflet, posterior leaflet and left ventricle wall. According to the tissue structure of the annulus 2.1, it is classified into the anterior fibrous portion and the posterior muscular portion. The chordae tendineae 2.4 starts from the papillary muscles 2.5 and attaches to the leaflets. It can prevent the anterior leaflet 2.2 and posterior leaflet 2.3 from collapsing into the left heart atrium.

The closure of normal mitral valve as shown in FIGS. 3 and 4. If the mitral valve closes completely, there is no gap between the anterior leaflet 2.2 and the posterior leaflet 2.3, the coaptation line 5 closes completely. If the closure of mitral valve 2 as shown in FIGS. 5 and 6, there is a gap in the coaptation line 5 and the blood will return from the left ventricle 3 to the left atrium 1 in systole because of the gap. (as indicated by the arrow in FIG. 5), and the backflow is called mitral regurgitation, mitral regurgitation decreases cardiac efficiency and causes heart failure.

Current surgical strategies for mitral regurgitation include normal or undersized annuloplasty, biological and mechanical mitral valve prosthesis implantation, etc. Most of these procedures need thoracotomy and open-heart surgery, but large trauma and low reliability will lead to 50% recurrence of mitral regurgitation within 5 years. The existing advanced minimally invasive treatment method is the MitraClip, clamping the midpoints of the anterior and posterior leaflet edges together to create two independent blood flow channels, reducing blood regurgitation, but this method still causes residual regurgitation.

CONTENTS OF THE INVENTION

The purpose of the present invention is to solve the problems existing in current treatment, and to provide an transapical implantation mitral valve balloon closure plate blocking body to repair mitral regurgitation. The balloon closure plate blocks regurgitation channel, reduces mitral regurgitation effectively. The invention provides an implantation method of the balloon closure plate simultaneously. The balloon closure plate is implanted in the orifice position between anterior and posterior leaflet with no need for thoracotomy and open-heart surgery by means of minimally invasive approach. It has little trauma to patients without residual regurgitation, and it gets high reliability.

In order to achieve the above objectives, the technical strategy to the invention of the transapical implantation mitral valve balloon closure plate blocking body is as follows: the transapical implantation mitral valve balloon closure plate blocking body includes a balloon closure plate, guide wires, guide ring and fixing plug, the fixing plug fixes at the apex of heart. The inside of balloon closure plate is a balloon and located at the closure position of the anterior and posterior leaflets; the hook is fixed in each of the right and left mitral annulus at the left and right leaflet joints, and the left and right guide wires go respectively through the same side hook and fixedly connected with the upper portion of the same side of the balloon closure plate, a guide ring is fixedly connected to the left lower portion and the right lower portion of the balloon closure plate, and the left and right guide wires go through the same side of the guide ring respectively and fixedly connected to the fixing plug; an infusion tube connects to the lower bottom edge of the balloon closure plate and the infusion tube is extended to the body via a fixing plug. The infusion tube connects the inside of the balloon closure plate. There is a check valve on the infusion tube and the gas and curable liquid can be filled in the balloon closure plate via the infusion tube.

Further, the bottom edge of the balloon connects to the end of the pull wire fixedly, the other end of the pull wire connects to the fixing plug fixedly.

The technical strategy of implantation of the transapical implantation mitral valve balloon closure blocking body is as follows: make a small incision which accesses to apex of heart on the left side of the chest, do a purse string procedure at the apex of heart, send the transapical cannula to the left ventricle via the center of purse string, tight the purse string and fix the transapical cannula, and there are more steps as follows:

A. Lead the guide wire through the hook which placed in the implantation catheter, the catheter is send to the commissure of the anterior and posterior leaflets via transapical cannula, insert the cannula into the mitral annulus and push the hook out of the implantation catheter by means of handspike; implanting the two hooks at the left and right sides of the commissures of the annulus separately; after the two hooks are implanted, take out the catheter, the two guide wires which connects to hooks extend out the body via the transapical catheter.

B. In vitro, the balloon closure plate, the guide ring, the check valve and a end of infusion tube is assembled as an integral part, the end of the guide wires connect to the same side of upper edge of the balloon closure plate and the other end connect to the same side of the guide ring; then the balloon closure plate is rolled and compressed into a cylinder, and place the cylinder into the implantation catheter, the transapical catheter enters in the left ventricle via transapical cannula, push the balloon plate and unfold it, the guide wires which connects to the guide ring extend out of the body via implantation catheter, finally, adjust and tighten the guide wires and make the left upper and right upper of the balloon closure plate alignment to the same side of the two hooks, the other end of the infusion tube extend out of the body via the implantation catheter.

C. Exit the implantation catheter, the balloon closure plate is filled with gas or curable liquid via the infusion tube, expand the balloon closure plate and form it up, finally, tight the infusion tube and the guide wires by fixing plug.

Further, in step B, the lower edge of the balloon closure plate connects to the end of the pull wire fixedly outside the body. After the balloon closure plate is fixed in the body, the other end of the pull wire extends to the body via the implantation catheter.

The advantages of the invention which adopt the above technical strategy are as follows: the balloon closure plate of the invention is made of elastic material which may be filled with gas or curable liquid. And it is implanted via a small incision on the left side of the chest, enters the left ventricle via the apex, and is placed and fixed at a regurgitant orifice position of the anterior and posterior leaflets closure point of the mitral valve. During diastole, the mitral valve opens, and blood flows from the left atrium to the left ventricle via two channels between the anterior or posterior leaflets and the balloon closure plate. During systole, the anterior and posterior leaflets close, and the edges of the leaflets and the balloon closure plate contact tightly together, thereby blocking the regurgitant channels of the mitral valve, and preventing the mitral regurgitation effectively. The balloon closure plate blocking body is simple in structure and highly reliable, the implantation method causes little trauma, and the residual regurgitation rate is low. The present invention treats diseases such as functional mitral valve regurgitation, and the success rate for repairing functional mitral regurgitation is more than 90%.

BRIEF DESCRIPTION OF THE DRAWINGS

The present invention will be further illustrated accompanying drawings and specific embodiments, but the scope of protection of the present invention is limited to that.

In the picture: 1—the left atrium, 2—the mitral valve, 2.1—the mitral annulus, 2.2—the anterior leaflet, 2.3—the posterior leaflet, 2.4—the chordae tendineae, 2.5—the papillary muscles, 3—the left ventricle, 4—the apex of heart, 5—the position of the closure of the anterior and posterior leaflets, 6—hooks, 6.1—barb, 6.2—connecting ring, 7—the balloon closure plate, 8—guide wire, 9—hook implantation catheter, 10—infusion tube, 11—closure plate implantation catheter, 12—fixing plug, 13—guide ring, 14—pull wire, 15—check valve.

DESCRIPTION OF THE PREFERRED EMBODIMENTS

Figure 1:
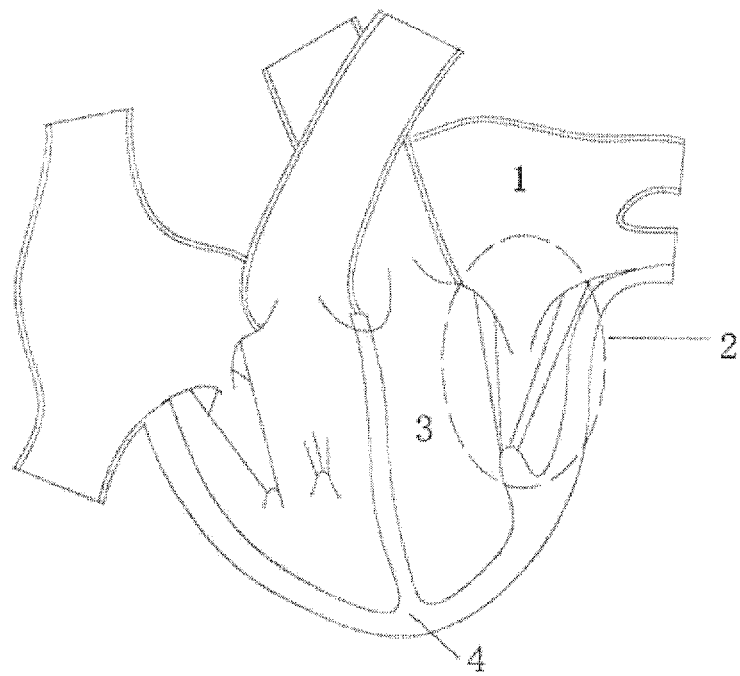
FIG. 1 shows the structure of the heart and the position of the mitral valve.
Figure 2:
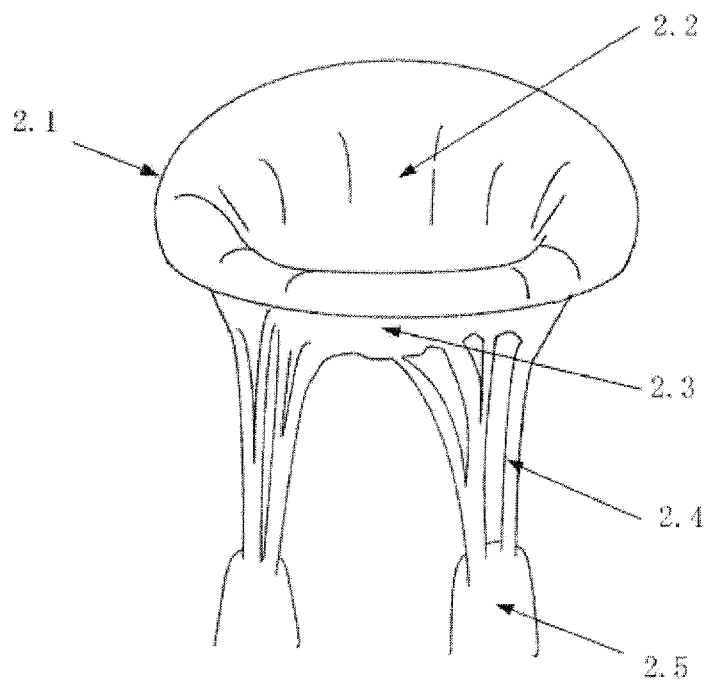
FIG. 2 shows an enlarged view of the tissue structure of the mitral valve in FIG. 1.
Figure 3:
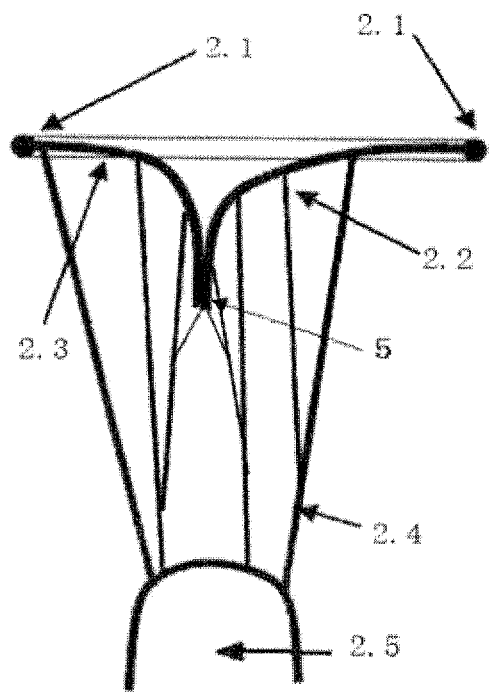
FIG. 3 shows a right view of the closed mitral valve in FIG. 2.
Figure 4:
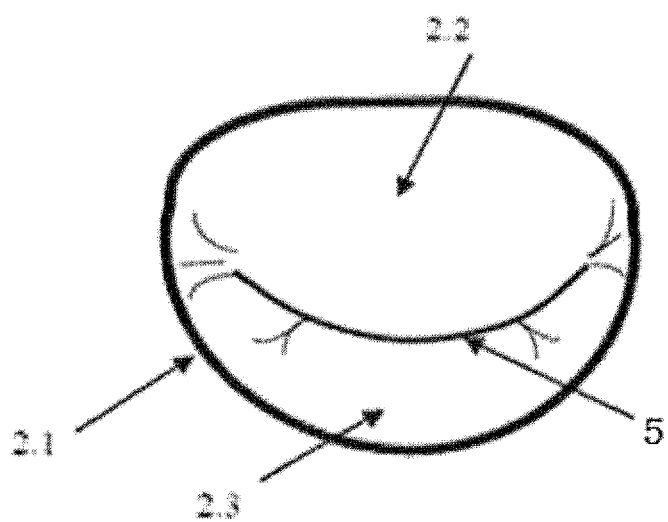
FIG. 4 shows an enlarged partial view of the atrium when the mitral valve closes in FIG. 2.
Figure 5:
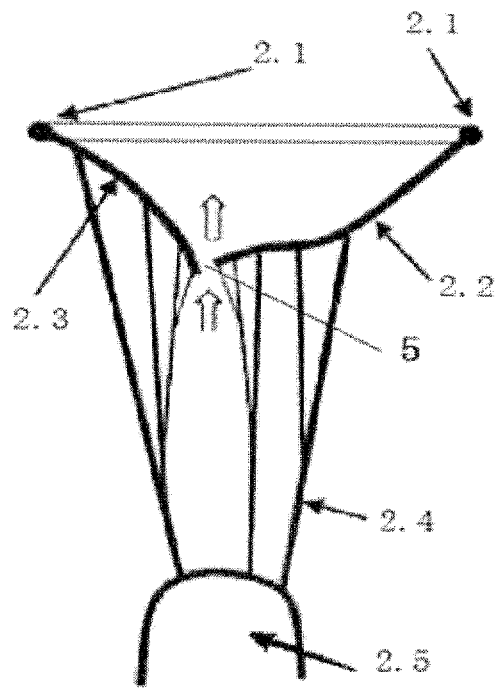
FIG. 5 shows a right view of the mitral valve regurgitation when the mitral valve closes insufficiently during systole in FIG. 2.
Figure 6:
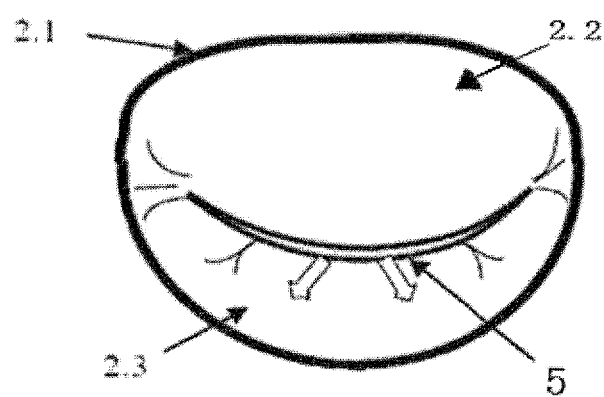
FIG. 6 shows an enlarged partial view of the atrium when the mitral valve closes insufficiently during systole in FIG. 2.
Figure 7:
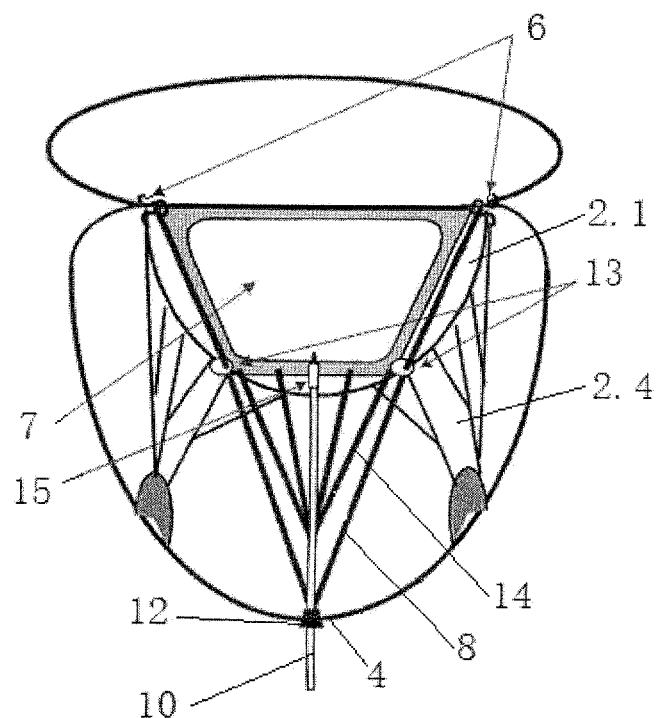
FIG. 7 shows a schematic view of a transapical implanted mitral valve balloon closure plate blocking body after implantation.

Referring to FIG. 7, the structure of a transapical mitral valve balloon closure plate blocking body of the invention consists of the hook 6, the balloon closure plate 7, the guide wire 8, the guide ring 13 and the fixing plug 12. The fixing plug 12 is implanted at the apex 4. There are 2 hooks 6, which are inserted at the left and right side of the mitral annulus 2.1 in the close position 5 of the mitral valve. There is a balloon inside the balloon closure plate 7, which is filled with gas or curable liquid, and the curable liquid is a substance that it is liquid when it is send into the balloon, but it will become solid after some time or after injecting a curing agent after being filled in the balloon. The longitudinal cross-sectional shape of the balloon closure plate 7 is an inverted isosceles trapezoidal structure, and the upper edge is longer than the bottom edge. The balloon closure plate 7 can be rolled and compressed into an elongated cylinder along the paralleled upper and bottom edge before it is filled with gas or curable liquid. The balloon closure plate 7 is place between the anterior leaflet and the posterior leaflets of the mitral valve 2 after it is implanted into the heart, and it is located at the close position 5 of the free edges of the anterior 2.2 and posterior 2.3 leaflets.

The balloon closure plate 7 is used to block the regurgitant gap caused by incomplete closure of the two leaflets. Two guide rings 13 are fixedly connected to the left lower and right lower position separately of the balloon closure plate 7. There are left and right guidewires 8 going through the hooks 6 on the same side separately. The guidewires 8 are fixedly connected to the upper side of the same side of the balloon closure plate 7. That is, the upper left position of the closure plate 7 is connected to the hook 6 on the left side via the first guidewire 8, and the right upper position of the closure plate 7 is connected to the hook 6 on the right side via the second guidewire 8. The left and right guidewires 8 respectively go through the same side of the guide ring 13 and extend downward to the apex 4 or the papillary muscles 2.5 and they are fixed by the fixing plug 12. That is, the first guidewire 8 goes through the left guide ring 13 and is pulled downward by the fixing plug 12. The second guide wire 8 threads through the guide ring 13 on the right side and is pulled downward by the fixing plug 12. The guide ring 13 is used to control the direction of the guide wire 8.

The lower bottom edge of the balloon closure plate 7 is fixedly connected to one end of the pull wire 14, and the other end of the pull wire 14 is fixedly connected to the fixed plug 12. There is a plurality of pull wires 14 in present invention. One end of the plurality of pull wires 14 are uniformly connected to the balloon closure plate 7 along the length direction of the lower bottom edge of the balloon closure plate 7. The other end of the plurality of pull wires 14 are fixedly connected to the fixing plug 12 and the balloon closure plate 7 is fixed by the pull wires 14. In this way, the balloon closure plate 7 is placed in the best position by means of hooks 6, pull wires 14 and fixing plugs 12.

The lower bottom edge of the balloon closure plate 7 connects to the infusion tube 10, the infusion tube 10 extends to the outside of the body through the fixing plug 12, and it connects the inside of the balloon closure plate 7, and a check valve 15 is fixed on the infusion tube 10, which can also be fixed on the junction of the infusion tube 10 and the balloon closure plate 7. The check valve 15 is used to allow gas or liquid to enter the balloon closure plate 7 only in one direction. The infusion tube 10 is a flexible medical hose for filling the inside of the balloon closure plate 7 with gas or curable liquid.

The balloon closure plate 7 is made of an elastic plastic material, such as medical silicone or latex. The hook 6 is made of an alloy material such as a nickel-titanium memory alloy material. The guide wire 8 and the pull wire 14 are made of ePTFE (expanded polytetrafluoroethylene) material. The fixing plug 12 is made of a blood-compatible material, and the blood-compatible material includes polyurethane or pericardium. The fixing plug 12 can lock the guide wire 8 and the pull wire 10 and fixes it at the apex 4 or the papillary muscle 2.5 position.

Figure 8:
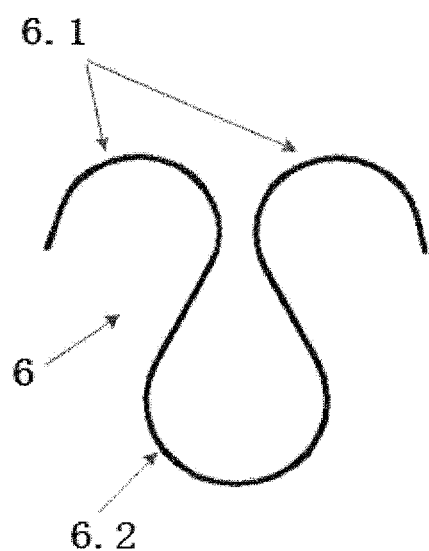
FIG. 8 shows an enlarged view of the structure of hooks in FIG. 7.

Referring to FIG. 8, the hook 6 is composed of two parts of two barbs 6.1 and a connecting ring 6.2. One end attaches to two barbs 6.1, and the other end connects to a connecting ring 6.2. When the hook is implanted, the barbs 6.1 are fixed on the annulus 2.1. The guide wire 8 threads through the connecting ring 6.2 and connects to the balloon closure plate 7 fixedly, and the balloon closure plate 7 and the hook card 6 are fixed by the guide wire 8.

Figure 9:
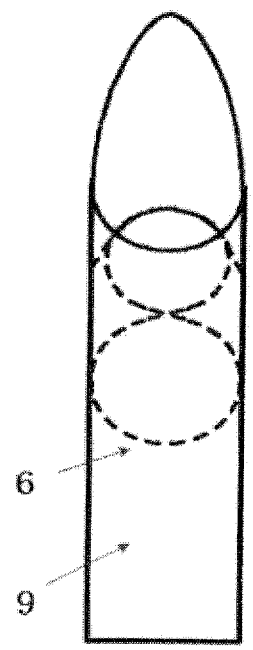
FIG. 9 shows a schematic view of the hook in the implantation catheter in FIG. 8.
Figure 10:
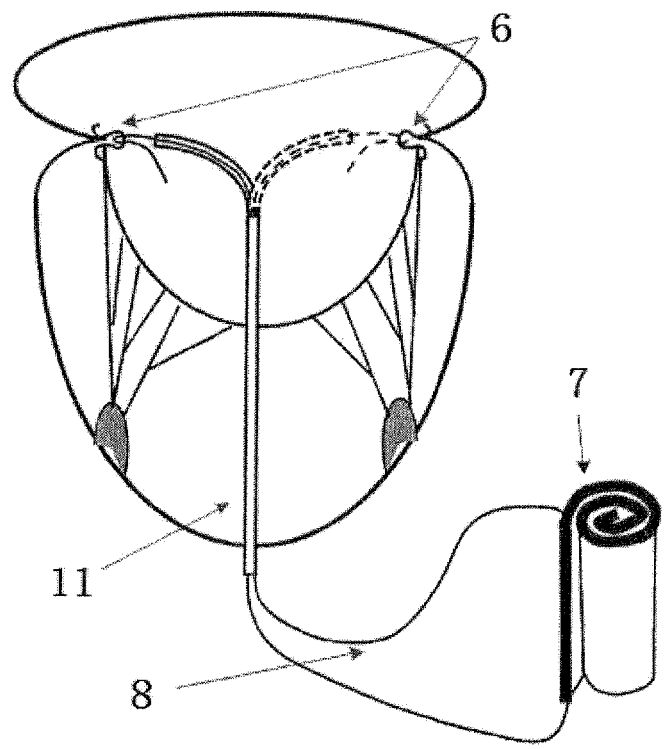
FIG. 10 shows a schematic view of the state of a transapical mitral valve balloon closure plate blocking plate.

Referring to FIG. 9, before the hook 6 is implanted in the heart, the hook 6 is first implanted into the hook implantation catheter 9. The inner diameter of the hook implantation catheter 9 is adapted to the outer diameter of the connecting ring 6.2 of the hook 6. When the hook 6 is put in, the hook 6.1 is slightly bent and then inserted into the front end of the hook implantation catheter 9.

Referring to FIGS. 1-10, a method for implanting the mitral valve balloon closure plate blocking body into a heart is as follows.

Step 1: First, make a small incision in the left apex of the chest which straight in the apex 4 and perform a purse-string operation at the apex 4 to insert the apical cannula into the left ventricle 3 from the purse, tighten the purse, and fix the apical cannula.

Step 2: In vitro, two guide wires 8 are respectively put on the connecting ring 6.2 of the hook 6, and two hooks 6, which are respectively connected with the guide wire 8 on the connecting ring 6.2, are respectively implanted on the left and right side of the mitral annulus 2.1 of the closure position of the anterior and posterior leaflets. The detailed method is as follows: Firstly, the first guide wire 8 is put on the connecting ring 6.2 of the first hook 6, and then the first hook 6 is send in the hook implantation catheter 9, loosen the hemostatic forceps of the transapical cannula and push the hook implantation catheter into the left ventricle 3 to reach the position of the annulus 2.1 of the both ends of the gap between the anterior leaflet 2.2 and posterior leaflet 2.3 via the transapical cannula of the incision in the left chest. Withdraw the first hook 6 from the front end of the hook implantation catheter, and the barb 6.1 is pushed out and deployed because of its elasticity so that it can insert into the left end of the mitral annulus 2.1. As the same way, the second guide wire 8 is put on the connecting ring 6.2 of the second hook 6, and then the second hook 6 is send in the hook implantation catheter 9, loosen the forceps of the apical cannula and push the hook implantation catheter into the left ventricle 3. Insert the barb 6.1 of the second hook 6 to the right end of the mitral annulus 2.1. In this way, exit the hook implantation catheter after the two hooks 6 are implanted. Both ends of all guide wires 8 which tread through the hook 6 are led to the outside the body through the transapical catheter, and the transapical catheter is clamped with a forceps to prevent bleeding of the heart.

Step 3: In vitro, the left lower portion of the balloon closure plate 7 is fixedly connected to a left guide ring 13, and the right lower portion is fixedly connected to a right guide ring 13. One end of the plurality of pull wires 14 is uniformly fixedly connected to the lower bottom edge of the balloon closure plate 7, and the middle of the lower bottom edge of the balloon closure plate 7 is fixedly connected to one end of the infusion tube 10, and the check valve 15 is fixed on the junction of the infusion tube 10 and the balloon closure 7. The balloon closure plate 7, the one-way valve 15, the end of the pull wire 14, the end of the infusion tube 10, and the two left and right guide rings 13 are integrated together. Alternatively, the lower edge of the balloon closure plate is uniformly connected with the pull wire 14, and the left and right lower portions are fixed with the guide ring 13, and the infusion tube 10 and the check valve 15 are formed to form an assembly, while the balloon closure plate 7 is manufactured.

One end of each guide wire 8 which is extended outside of the body is respectively fixedly connected with the upper portion of the same side of the balloon closure plate 7, and the other end of each guide wire 8 is respectively pass through the same side guide ring 13. That is, one end of the first guide wire 8 is fixedly connected to the left upper portion of the balloon closure plate 7, and the other end of the first guide wire 8 goes through the left guide ring 13 fixed on the flexible closure plate 7, and one end of the second guide wire 8 is fixedly connected to the upper right portion of the balloon closure plate 7, and the other end of the second guide wire 8 goes through the right guide ring 13 fixed on the flexible closure plate 7. The balloon closure plate 7 is then tightly rolled and compressed into an elongate cylindrical body along its own parallel upper or lower bottom edge, and the curled balloon closure plate 7 is put into the closure plate implantation catheter 11 together with the guide ring 13, the check valve 15, one end of the infusion tube 10 and one end of the pull wire 14. To loosen the forceps of the transapical cannula, the closure plate implantation catheter 11 is implanted from a small incision on the left side of the chest and into the left ventricle 3 via the transapical cannula.

Step 4: The balloon closure plate 7 is pushed out of the closure plate implantation catheter 11, and the balloon closure plate 7 is deployed inside the left ventricle 3. In the meantime, the other end of the infusion tube 10, the other end of the pull wire 14, and the guide wire 8 which goes through the guide ring 13 all extend from the apex 4 through the balloon closure plate implantation catheter 11 outside the body. Adjust the outer ends of the two guide wires 8 which goes through the guide ring 13 and tighten the guide wire 8 so that the left upper portion and the right upper portion of the balloon closure plate 7 are respectively located on the same side of the hook 6 to fix the balloon closure plate 7. The pull wire 14 is adjusted so that the lower edge of the balloon closure plate 7 is tightened by the other end of the pull wire 14 simultaneously.

Step 5: Exit the balloon closure plate implantation catheter 11, remove the transapical cannula, and tighten the purse to prevent bleeding from the heart. The extracorporeal ends of the infusion tube 10, the guide wire 8 and the pull wire 14 go through the fixing plug 12. The fixing plug 12 has a small end that protrudes into the apex 4 and has a large area at the other end, which is close to the surface of the apex 4. There is a hole in the middle of the fixing plug 12. The infusion tube 10, the guide wire 8 and the pull wire 14 are dragged from the central hole of the fixing plug 12. The fixing plug 12 is pushed toward the apex 4 and the purse is released. After the fixing plug 12 is placed on the apex 4, the purse is tightened and fixed. Lock pull wire 14 and the guide wire 8 fixedly by the fixing plug 12 after adjusting tension of the pull wire 14 and the guide wire 8 to be optimal.

Step 6: The gas or the curable liquid is introduced into the balloon closure plate 7 through the infusion tube 10 to inflate and shape it. The infusion tube 10 is locked by the fixing plug 12, and the excess infusion tube 10, the pulling wire 14 and the guide wire 8 on the outside of the fixing plug 12 are cut off.

Step 7: The small incision on the left side of the chest was sutured, and the entire process of the balloon closure plate blocking body was completed.

During diastole, the mitral valve 2 opens and blood flows from the left atrium 1 into the left ventricle 3 via two channels between the anterior leaflet 2.2, the posterior leaflet 2.3, and the balloon closure plate 7. During systole, the anterior 2.2 and posterior 2.3 close, and the edges of the leaflets and the balloon closure plate 7 fit tightly together, thereby blocking a regurgitant gap of the mitral valve 2, and preventing regurgitation of the mitral valve 2 effectively.

The invention claimed is:

1. A transapical implantation mitral valve balloon closure plate blocking body comprising a balloon closure plate, left and right guide wires, a guide ring and a fixing plug, wherein:
   the fixing plug is adapted to be fixed at an apex of a heart;
   an inside of the balloon closure plate is a balloon and is adapted to be located at a closure position of the anterior and posterior leaflets of the heart;
   a pair of hooks adapted to be fixed in each of the right and left mitral annulus at the left and right leaflet joints of the heart, respectively;
   the left and right guide wires are respectively passed through the same side hook and fixedly connected with an upper portion of the same side of the balloon closure plate;
   the guide ring is fixedly connected to a left lower portion and a right lower portion of the balloon closure plate, and the left and right guide wires pass through the same side of the guide ring respectively and fixedly connected to the fixing plug;
   an infusion tube connects to a lower bottom edge of the balloon closure plate and is configured to extend to outside the patient's body via a fixed plug; wherein
   the infusion tube connects with the inside of the balloon closure plate; and
   a check valve is provided on the infusion tube whereupon a gas and curable liquid can fill in the balloon closure plate via the infusion tube.

2. The transapical implantation mitral valve balloon closure plate blockage body of claim 1, further comprising a pull wire, wherein the lower bottom edge of the balloon closure plate connects to the end of the pull wire fixedly, and the other end of the pull wire connects to the fixed plug fixedly.

3. The transapical implantation flexible mitral balloon closure plate blocking body of claim 1, wherein there are a plurality of pull wires, wherein one end of the plurality of pull wires are uniformly connected to the balloon closure plate along a length direction of the lower bottom edge of the balloon closure plate and the other end of the plurality of pull wires are connected to and fixed in the fixing plug.

4. The transapical implantation flexible mitral balloon closure plate blocking body of claim 1, wherein the longitudinal section of the balloon closure plate is an inverted isosceles trapezoidal structure, and the balloon closure plate can be rolled into a cylinder along the upper edge or the bottom edge.

5. The transapical implantation flexible mitral balloon closure plate blocking body claim 1, wherein the balloon closure plate is made of an elastic plastic, the hook is made of an alloy material, the left and right guide wires are made of an expanded polytetrafluoroethylene material, and the fixing plug is made of a blood compatible material.

6. The transapical implantation flexible mitral balloon closure plate blocking body of claim 1, wherein the hook consists of two parts, a barb and a connecting ring, and the left guide wire or the right guide wire goes through the connecting ring.

7. A method for repairing mitral regurgitation of a patient in need thereof, comprising:
   (A) providing an apical implantation mitral valve balloon closure blocking body as claimed in claim 1;
   (B) from a small incision which connects an apex of the patient's heart on the left side of the chest; performing a purse surgery at the apex of the heart to form a purse;
   (C) sending a transapical cannula to the left ventricle via the purse;
   (D) tightening the purse and fixing the transapical cannula;
   (E) leading the left and right guide wires through the pair of hooks which are placed in an implanted catheter;
   (F) sending the implanted catheter to the commissures of the anterior and posterior leaflets via the transapical cannula in the left ventricle;
   (G) pushing the pair of hooks out of the implanted catheter using a handspike;
   (H) inserting the pair of hooks in the mitral annulus;
   (I) implanting the pair of hooks at the left and right commissures of the annulus separately;
   (J) after the pair of hooks are implanted, removing the implanted catheter, whereupon the left and right guide wires which go through the pair of hooks extend out the body via the transapical catheter,
   (K) In vitro assembling the balloon closure plate, the guide ring, the check valve and the end of the infusion tube as an integral part, wherein the end of the left and right guide wires connect to the same side of upper edge of the balloon closure plate and the other end connects to the same side of the guide ring;
   (L) rolling up the balloon closure plate as a cylinder, and compressing the cylinder into the implanted catheter;
   (M) introducing a transapical catheter in the left ventricle via the transapical cannula, and pushing the balloon plate and unfolding it, whereupon the left and right guide wires which go through the guide ring extend out of the body via the implanted catheter;
   (N) tightening the left and right guide wires and bringing the left upper and right upper portions of the balloon closure plate into alignment to the same side of the two hooks, whereupon the other end of the infusion tube extends out of the body via the implanted catheter;
   (O) removing the implanted catheter and filling the balloon closure plate with a gas or curable liquid via the infusion tube, expanding the balloon closure plate and forming it up; and
   (P) tightening the infusion tube and the guide wires by the fixing plug.

8. The implantation method of claim 7, wherein in step (K), the lower edge of the balloon closure plate connects to the end of the pull wire fixedly outside the patient's body; and after the balloon closure plate is fixed in the patient's body, the other end of the pull wire is extended to the patient's body via the implanted catheter.

9. The implantation method of claim 7, wherein in step (E), one end of the left and right guide wires goes through the connecting ring of a respective hook of the pair of hooks, and the barb of the respective hook is inserted into the mitral valve annulus of the heart.

* * * * *